(12) United States Patent
Pragnon et al.

(10) Patent No.: US 7,491,505 B2
(45) Date of Patent: Feb. 17, 2009

(54) METHOD FOR ANALYZING TUMOR AGGRESSIVITY COMPRISING MEASUREMENT OF POLYMERIZED ACTIN

(75) Inventors: Christelle Pragnon, Savonniere (FR); Valérie Polard, Alfortville (FR); Frédéric Subra, Paris (FR); Christian Auclair, Paris (FR)

(73) Assignees: Bioalliance Pharma, Paris (FR); Ens Cachan, Cachan (FR); Centre National de la Recherche Scientifique-CNRS, Paris (FR)

( * ) Notice: Subject to any disclaimer, the term of this patent is extended or adjusted under 35 U.S.C. 154(b) by 0 days.

(21) Appl. No.: 10/539,406

(22) PCT Filed: Dec. 18, 2003

(86) PCT No.: PCT/FR03/03802

§ 371 (c)(1),
(2), (4) Date: Nov. 23, 2005

(87) PCT Pub. No.: WO2004/057337

PCT Pub. Date: Jul. 8, 2004

(65) Prior Publication Data

US 2006/0166289 A1 Jul. 27, 2006

(30) Foreign Application Priority Data

Dec. 19, 2002 (FR) ................................. 02 16188

(51) Int. Cl.
*G01N 33/53* (2006.01)
*G01N 33/574* (2006.01)

(52) U.S. Cl. ........................................ 435/7.8; 435/7.23

(58) Field of Classification Search ....................... None
See application file for complete search history.

(56) References Cited

U.S. PATENT DOCUMENTS 5,851,786 A 12/1998 Johnson

FOREIGN PATENT DOCUMENTS

| WO | 99/11814 A | 3/1999 |
|---|---|---|
| WO | 01/41815 A | 6/2001 |
| WO | 01/71356 A | 9/2001 |

OTHER PUBLICATIONS

Tellam et al. Increased Actin Nucleating Activity in Tumerigenic Cells; Biochemical and Biophysical Research Communications, vol. 134, No. 3 (1986) pp. 1284-1290.*
Malicka-Blaszkiewicz et al. Actin Content and Polymerization in Tumour, Liver and Serum of the Hepatoma Morris 5123 Tumour Bearing Rats; Materia Medica Polona, vol. 27, No. 3 (1995) pp. 115-118.*
Menu et al. The F-Actin Content of Multiple Myeloma Cells as a Measure of Their Migration; Ann. N.Y. Acad. Sci., vol. 973 (2002) pp. 124-134.*
Damiano, J. S. et al. (2001). "Cell adhesion mediated drug resistance (CAM-DR) protects the K562 chronic myelogenous leukemia cell line from apoptosis induced by BCR/ABL inhibition, cytotoxic drugs, and gamma-irradiation." Leukemia 15(8):1232-9.
Faute, M. A. et al. (2002). "Distinctive alterations of invasiveness, drug resistance and cell-cell organization in 3D cultures of NCF-7, a human breast cancer cell line, and its multidrug resistant variant." Clin Exp Metastasis 19(2): 161-8.
Dugray, A. et al. (2001). "Rapid generation of a tetracycline-inducible BCR-ABL defective retrovirus using a single autoregulatory retroviral cassette." Leukemia 15: 1658-62.
Fradelizi, J. et al. (2001). "ActA and human zyxin harbour Arp2/3-independent acting polymerization activity." Nat Cell Biol 3(8) 699-707.
Lopes, E. C. et al. (2001), "Dissimilar invasive and metastatic behavior of vincriatine and doxorubicin-resistant cell lines derived from a murine T cell lymphoid leukemia." Clin Exp Metastasis 19(4): 283-90.
Machesky, L. M. et al. (1999). "Scar, a WASp-related protein, activates nucleation of actin filaments by the Arp2/3 complex." Proc Natl Acad Sci U S A 96(7): 3739-44.
Mitsumoto, M. et al. (1998). "Emergence of higher levels of invasive and metastatic properties in the drug-resistant cancer cell lines after the repeated administration of cisplatin in tumor-bearing mice." J Cancer Res Clin Oncol 124(11): 607-14.
Nakamura, K. et al. (2002). "Characterization of murine melanoma cell lines by their mortal malignancy using an experimental metastatic model." Life Sci 70(7): 791-8.

\* cited by examiner

*Primary Examiner*—Jon P Weber
*Assistant Examiner*—Paul C. Martin
(74) *Attorney, Agent, or Firm*—Arent Fox LLP

(57) ABSTRACT

The invention concerns a method for analyzing tumor agressivity of cancer cells comprising measurement of the amount of stationary polymerized actin in a lysate of said cells. Advantageously, the measurement of the amount of stationary actin is carried out by fluorescence static polarization.

10 Claims, 3 Drawing Sheets

METHOD FOR ANALYZING TUMOR AGGRESSIVITY COMPRISING MEASUREMENT OF POLYMERIZED ACTIN

CROSS-REFERENCE TO RELATED APPLICATION

This application is a National Stage entry of International Application Number PCT/FR2003/003802, filed Dec. 18, 2003. The disclosure of the prior application is hereby incorporated herein in its entirety by reference.

The objective of the present invention is a diagnostic or predictive test in the cancer field. More precisely, the invention concerns a method based on the direct measurement of the quantity of polymerized actin in the steady state in a non-purified cellular lysate, as an indicator of both tumor aggressivity and sensitivity to anti-tumor treatment.

Based on one preferred form of implementation, the invention method is remarkable in that, apart from the cellular extract and the fluorescent actin, no supplementary purified protein addition is necessary to simultaneously reveal discrimination between sensitive or resistant cells and cells that are or are not potentially aggressive.

The actin cytoskeleton is a protein structure that is essential to cellular survival. Notably, it enables the cell to maintain its shape and its binding ability, to migrate, to communicate with adjacent cells. The cytoskeleton is an extremely dynamic structure, in a perpetual state of alteration.

The dynamic properties of the cytoskeleton enable the cell to communicate with the external environment and to migrate to form metastases, for example. These two properties are at the origin of tissue cohesion.

The dynamic properties of the cytoskeleton make its study extremely difficult.

Many mechanisms for the regulation of actin polymerization have been described in earlier work, among which can be cited mechanisms dependent either on the Arp2/3 complex, or by the intervention of the family of proteins bound to Ena/VASP.

Thus, the Arp2/3 complex, consisting of at least seven protein sub-units, is regulated by the members of the Wiskott-Aldrich (WASP) syndrome family of proteins to activate the nucleation of the Y-structured actin filaments (Machesky, Mullins et al. 1999).

For Ena/VASP, this is the family of proteins whose prototype is zyxin, among which can be mentioned LPP (LIM-containing lipoma preferred partner), and TRIPE (thyroid receptor-interacting protein-6), characterized by the fact that they possess a rich proline domain followed by three LIM domains. The proteins belonging to this family interact with the proteins from the Ena/VASP family among which can be mentioned VASP (Vasodilator stimulated phosphoprotein), Ena (with the drosophila), Mena (equivalent of the Ena protein in mammals) and Ev1. Although these latter two families of proteins are clearly involved in the regulation of this mechanism of actin polymerization, the sequence of events responsible is not clearly explained (Fradelizi, Noireaux et al. 2001).

It seems that a single cell can contain several systems for actin polymerization, each being responsible for a particular type of actin structure.

The dynamic properties of the cytoskeleton render its analysis extremely complex, taking into account the different protein systems involved in the process of actin polymerization and de-polymerization. If the binding and resistance properties are related (Damian, Hazlehurst et al. 2001; called Faute, Laurend et al. 2002), the invasive properties of cancerous cells differ according to their resistance to anti-cancer treatments (Lopes, Ernst et al. 2002). In vivo, the resistant cells seem to have a greater invasive power (Mitsumoto, Kamura et al. 1998).

Thus, the study of only one of the two mechanisms in a purified system in vitro may be incomplete for judging the cellular potential of actin polymerization of an extract from a cell line or from a biological sample.

The research work carried out within the framework of the present invention has now made evident a net correlation between the measurement of the quantity of polymerized actin in the steady state on the one hand, and tumor aggressivity on the other.

The present invention thus has the objective of offering a simple and effective diagnostic or predictive method for tumor aggressivity and the sensitivity of a subject to anti-cancer treatment. This objective is attained by means of a method which consists of measuring the quantity of polymerized actin in the steady state in a cellular extract from a sample taken from a subject.

More specifically, the invention has the objective of creating a method of analysis of tumor aggressivity in cancerous cells from a subject consisting of the measurement of the quantity of polymerized actin in the steady state in a cellular extract from the subject.

Advantageously, the cellular extract is a lysate of the said cancerous cells.

Tumor aggressivity is understood to mean the invasive character of a cancer or a cancerous cell line, that is both its metastatic potential as well as the rapidity with which a primary tumor develops and grows. Tumor aggressivity is also understood to mean oncogenicity, that is, the capacity of a cell line to result more or less efficiently in the appearance of a tumor after subcutaneous injection into a murine model likely to receive this line. Tumor aggressivity is also understood to mean the absence of sensitivity to anti-cancer treatment.

The measurement taken on the cellular extract from the subject is compared to one or more specific reference values of tissue analyzed in the case of biological samples, or phenotype specifics, in the case of cell lines.

The quantity of polymerized actin corresponds to the sum of all the F-form actin. This sum depends on the total quantity of actin, regardless of its form, form F or form G, but above all, on the whole of the mechanisms for regulating polymerization and de-polymerization.

Actin F is understood to mean the more or less long polymers of globular actin (actin G). The formation of actin F is a dynamic phenomenon, very precisely regulated by several different mechanisms. Actin F may suffer in a concomitant manner a phenomenon of polymerization of globular actin at one extremity of the filament and a phenomenon of depolymerization at the other extremity.

An objective of the present invention is to be freed of the various paths of the regulation of actin polymerization by utilizing an integrated system.

This objective is attained according to the invention by means of a measurement of the quantity of polymerized actin in the steady state which takes into account the results of all the mechanisms for regulating the polymerization and de-polymerization of the actin filaments, and more precisely, both the mechanisms of stimulation as well as the mechanisms of inhibition of polymerization and de-polymerization. The steady state results from the equilibrium among all these mechanisms for regulating actin polymerization at one extremity of the actin filament and depolymerization at the other extremity.

In an advantageous manner, the measurement of polymerized actin in the steady state does not necessitate a measurement of an expression of a protein (for example, zyxin or one of the proteins of the Arp2/3 complex or one of the proteins from the Ena/VASP family) and does not necessitate the protein purification step or the addition of solid reactants (balls, for example).

The present invention enables a measurement of the quantity of polymerized actin in the steady state for a non-purified cellular extract, where all the activation/inhibition paths for the actin polymerization and de-polymerization processes are integrated.

Thus, the quantity of polymerized actin in the steady state is understood to mean the quantity of polymerized actin when equilibrium between the actin polymerization at one extremity of the filaments and the depolymerization at the other extremity is attained. As indicated previously, the steady state is the result of all the paths for regulating the actin polymerization.

The measurement of the quantity of actin in the steady state can be accomplished by any technique known to a person skilled in the art, such as, for example, the static fluorescence polarization technique, also known as static fluorescence anisotropy.

Anisotropy and polarization are two values related mathematically, and thus easily interchanged. They describe the same phenomenon. Fluorescence polarization permits a study of the interactions between molecules by measuring the changes in the size of fluorescent molecules in solution. This measurement is correlated with the size of the fluorescent molecule or the fluorescent molecular complex. In this case, the fluorescent molecule is an actin monomer (or actin G) bound to a fluorochrome, in the case of Alexa 488, which is incorporated in the actin filaments (actin F) in the course of the polymerization.

Thus, according to one highly preferred method of implementation, the measurement of the quantity of actin in the steady state of the invention's method of analysis is realized by static fluorescence polarization in the presence of actin monomers bound to a fluorochrome, which are incorporated into the actin filaments (actin F) formed in the course of the endogenous actin polymerization of the lysate.

In this form of implementation, the actin monomers bound to a fluorochrome are added to a cellular lysate in a ratio ranging between $1/80^{th}$ and $1/1600^{th}$ in relation to the quantity of endogenous actin.

The result of the test is a plateau fluorescence anisotropy value (<<STAFI>>) corresponding to the quantity of polymerized actin in the steady state and an apparent constant ($K_{obs}$) for actin polymerization resulting from the progressive incorporation of marked actin monomers over time until attainment of the steady state, that is the plateau of the curve.

By use of the GraphPad Prism® version 3 Software (GraphPad Software, Inc., San Diego, Calif.), for biostatistics, curve fitting, and scientific graphing, the experimental data are used to generate a curve adjusted to a 1st order equation such that:

$$Y = \Delta mA \max(1-e^{-k \cdot t}) \text{ where}$$

Y=the anisotropy value measured at time t $\Delta mA$ max=<<STAFI>>, the maximum ordinate value at equilibrium K=the constant $K_{obs}$ t=the time in seconds.

To predict a level of tumor aggressivity and sensitivity to an anti-cancer treatment, these two values must be compared either to specific reference values of the tissue analyzed in the case of the biological samples, or specifics of the phenotype, in the case of cell lines.

A sample from a very aggressive cancer specimen, that is, one presenting either an invasive character or an oncogenic character or again, having lost the characteristic of sensitivity to anti-cancer treatments, will present a STAFI and a $K_{obs}$ which is lower than the reference value, that is, the value obtained from similar samples that are only slightly or non-aggressive.

For example, the normal plateau value for fluorescence anisotropy (<<STAFI>>=delta mA max) for a low-invasive line of melanoma (B16F0) is 47 mA ($K_{obs}$=0.07). A line derived from it, described moreover as very invasive (B16F10) (Nakamura, Yoshikawa et al. 2002), presents a STAFI value of 37 mA ($K_{obs}$=0.02), distinctly lower that the value of the B16F0s. The <<STAFI>> and $K_{obs}$ values obtained from invasive cell lysates are distinctly lower than the values of the reference line (FIG. 3).

Another example is the comparison of the <<STAFI>> value of oncogenic lines with the value obtained from non-oncogenic parental cell lines taken as references. The <<STAFI>> value of oncogenic lines is distinctly lower than the value of non-oncogenic reference lines.

In the example of lines derived from NIH 3T3, the <<STAFI>> of the oncogenic line (NIH 3T3 EF) is equal to 35 mA compared to the non-oncogenic reference lines (NIH 3T3 and NIH 3T3 EF zyxin) for which the <<STAFI>> is equal to 65 and 57 mA respectively (FIG. 1).

The oncogenic line BAF3 bcr-abl and the non-oncogenic line BAF3 present <<STAFI>> values of 40 mA and 58 mA respectively. Repression of the fusion oncogenic expression, responsible for the oncogenicity of the BAF3 bcr-abl line, induces the restoration of the value of <<STAFI>> to a value close to the reference line <<STAFI>> i.e., 52 mA and 58 mA respectively (FIG. 2).

A last example is the comparison of the <<STAFI>> value of breast cancer cell lines more or less sensitive to anti-cancer treatment. The <<STAFI>> values of the two resistant lines (MCF7-MDR and MCF7-dox) are distinctly lower than the value of the sensitive line (MCF7) taken as a reference, i.e., 35 mA and 52 mA versus 71 mA (FIG. 4).

A preferred example of implementation of the method according to the invention includes the following steps:

the lysis of cancerous cells in non-denaturing conditions for the proteins and the elimination of cellular debris, the total protein dosage of the lysate, the addition of actin monomers bound to fluorochrome, the addition of substances required for endogenous actin polymerization and the protection of the lysate proteins, the measurement of the quantity of polymerized actin in the steady state in the lysate.

The present invention also aims to offer a method of identification of molecules likely to present an anti-cancer activity. Such a method consists of implementing the method of analysis of tumor aggressivity in the presence of a sufficient quantity of one or more molecules to be tested, and the determination of the capacity of the said molecule to restore a quantity of polymerized actin in the steady state corresponding that of non-aggressive cells.

The work carried out within the framework of the present invention resulted in the identification of molecules capable of restoring the <<STAFI>> value of aggressive cells to the level of that of non-aggressive cells. These molecules are likely to present an anti-cancer activity.

For example, the Jasplakinolide, added to the lysate of aggressive cells (NIH 3T3 EF) right at the time of the test, enabled the restoration of the <<STAFI>> value of these cells to a value near that of the <<STAFI>> of nononcogenic reference cells (NIH 3T3) (FIG. 5). Table 1 below summarizes the restoration of the value of delta mA max (<<STAFI>>, corresponding to the quantity of polymerized actin in the steady state) of oncogenic cells (NIH 3T3 EF, marked EF) to the level of the value of non-oncogenic cells (NIH 3T3) by the addition of the jasplakinolide (marked jaspla).

TABLE 1

| Cell lines | ΔmA max |
| --- | --- |
| NIH 3T3 EF | 30 |
| NIH 3T3 | 62 |
| NIH 3T3 BF + Jasplakinolide | 65 |

The invention again concerns the application of the method of analysis of tumor aggressivity previously described to:
the evaluation of the invasive character of the said cells;
the evaluation of the oncogenicity of the cells;
the prediction of the sensitivity of the said cells to an anti-cancer treatment; the anti-cancer treatment consists for example of radiotherapy or chemotherapy.

Sensitivity to anti-cancer treatment is understood to mean both the absence of resistance to medication based on the MDR system (multi-drug resistance) bound to pump mechanisms of the P-gp family of proteins, as well as the capacity of cancerous cells to go into apoptosis. These two phenomena can be in response to an anti-cancer treatment consisting of radiotherapy or chemotherapy.

The invention is also directed at a kit for a diagnostic or predictive test of tumor aggressivity, and more especially, for the measurement of the quantity of polymerized actin in the steady state for the evaluation of tumor aggressivity in a biological sample.

Such a kit includes:
a cell re-suspension medium for the lysis of cells,
the substances necessary for endogenous actin polymerization and the protection of the lysate proteins,
the actin monomers bound to a fluorochrome,
an actin polymerization solution,
a general actin solution,
possibly the extract of aggressive and non-aggressive reference cells.

Other advantages and characteristics of the invention will appear in the examples which follow, in which reference will be made to the appended drawings where;

I. METHODS

Figure 1:
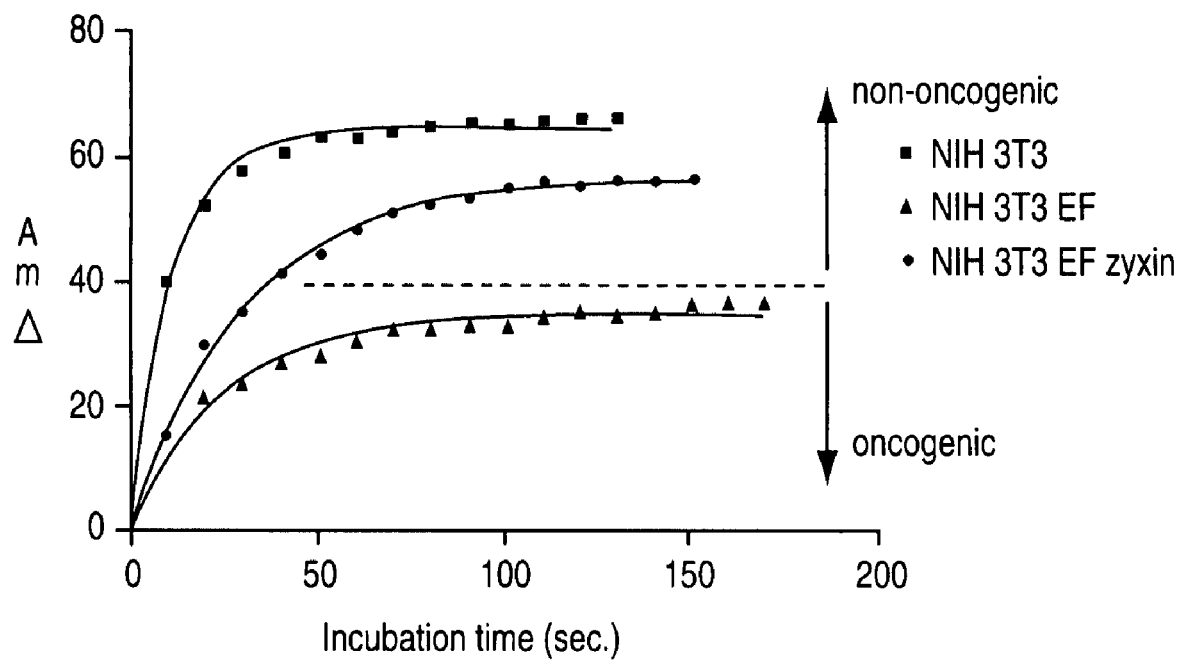
FIG. 1 illustrates the measurement of actin polymerization in the steady state (<<STAFI>>=delta mA max) in murine parental member cell lines, both non-oncogenic (NIH 3T3 and NIH 3T3 BF zyxin) and oncogenic (NIH 3T3 EF).

The technique of fluorescence polarization, also called static fluorescence anisotropy enables the obtaining of a value dependent on the size of the fluorescent molecule and the number of fluorescent molecular complexes. That is, by the addition of a small proportion of fluorescent monomer actin in a cellular extract, these monomers will be incorporated in the actin filament during polymerization, which will result in an increase in the anisotropy value up to an apparent plateau corresponding to equilibrium between the polymerization and de-polymerization of the actin filaments containing the fluorescent monomers. The level of this plateau, called <<STAFI>> reflects the quantity of F at the steady state, that is, the cell binding potential, and the speed of reaching the plateau depends on the rapidity with which these filaments are formed. These two parameters are the indices of tumor aggressivity.

Method of cell lysis: For cells in culture, the cells might have to be trypsinized before being washed (washing solution: 135 mM NaCl, 2.7 mM KCl, 11.9 nM NaHCO$_3$, 0.36 mM NaH$_2$PO$_4$, 2 mM MgCl$_2$, 0.2 mM EGTA, 5.5 mM glucose, 0.3% albumin, pH>6.5). The cells are placed in suspension in a sonication solution (10 mM Tri-HCl, pH 7.5, 10 mM EGTA and 2 mm MgCl$_2$+Roche protease inhibitors) at a rate of 50.10$^6$ cells/ml and sonicated on ice, at a rate of 10 runs of 10 seconds separated by 30-second pauses. The lysate is centrifuged for 30 min at 8000 rpm at 4° C. and filtered at 0.45 μm. The concentration in total proteins of the lysate is measured by the Bradford method, to be adjusted to 2 mg/ml with a sonication solution. 0.4 mM final of ATP and DTT are added to constitute the cellular lysate to be tested.

The actin monomer solution bound to a fluorochrome is prepared in the following manner: the Alexa 488 actin stock solution (Molecular Probes) (7.3 mg/ml) is diluted to 1:200th in a G solution (5 mM Tri pH 8.1, 0.2 mM CaCl$_2$ 0.2 mM DTT, 0.2 mM ATP) supplemented with 10% sucrose and ultracentrifuged at 35,000 rpm, 120 min, at 4° C. in order to eliminate possible actin filaments. This solution of marked actin monomers is stored at −80° C. in aliquots.

At the time of the test, the solution of marked actin monomers is diluted to 1/3 in G solution. The apparatus used is a Beacon® 2000 Fluorescence Polarization System (Invitrogen Corporation, Carlsbad, Calif.) fluorescence polarization spectrometer. Introduce into the Beacon® tube 167 μl of solution G and 3 μl of marked actin monomer solution diluted beforehand. After stabilization of the actin monomer anisotropy value at about 110 mA, add 4 μl of polymerization solution (2.5 M KCl, 50 mM MgCl$_2$, 25 mM ATP) and 20 μl of the cellular extract to be tested at 2 mg/ml. The fluorescence anisotropy value is recorded over a period of about 200 seconds. The data are processed with the GraphPad Prism® version 3.0 software (GraphPad Software, Inc., San Diego, Calif.), for biostatistics, curve fitting, and scientific graphing. The fluorescence anisotropy value of the marked actin monomers alone (about 110 mA) is removed from the values that follow.

The whole set of cell lines is cultivated at 37° C. in a humid atmosphere containing 5% CO$_2$. They are maintained in a DMEM or RPMI (Gibco) medium, supplemented with 10% newborn veal serum or fetal veal serum (Gibco) and antibiotics (penicillin at 100 UI/mL and streptomycin at 100 μg/mL).

The NIH-3T3 line is a line of non-oncogenic murine fibroblasts.

The NIH-3T3-EF line is a tumor line derived from the precedent and contains a coding ADNc for the fusion oncogene EWS-FLI in its genome. The expression of this protein is selected with the help of 2.5 μg/mL of puromycin.

The NIH-3T3-EF-zyxin line is a line derived from the precedent, which has lost its oncogenic character following transformation by a coding ADNc for the human zyxin protein. The expression of this protein is selected with the help of geneticin.

The BAF3 line is a pre-lymphocytic murine line. It is maintained in the presence of IL3.

The BAF3 Bcr-Abl line is a line derived from the precedent containing a coding ADNc for the fusion oncogene Bcr-Abl, the expression of which can be suppressed by doxicycline. When this line is cultivated in the absence of doxicycline and IL3, the oncogene is expressed, and it is then marked BAF3 Bcr-Abl. When this line is cultivated in the presence of doxicycline and IL3, the fusion oncogene is no longer expressed, and it is marked BAF3 bcr-abl'-(Dugray, Geay et al. 2001).

The B16F0 line is a murine melanoma line with a weak metastatic potential (Nakamura, Yoshikawa et al. 2002).

The B16F10 line is a line derived from the precedent having acquired a strong metastatic potential as a result of 10 successive selections in a syngeneic murine model of pulmonary metastases (Nakamura, Yoshikawa et al. 2002). The MCF7 line is a line of weakly oncogenic human mammary carcinoma.

The MCF7-Dox line is a line derived from the precedent, rendered resistant to doxorubicin by the regular addition of 10 μM of doxorubicin in a culture medium.

The MCF7-MDR line is a line derived from the MCF7 line, containing an ADNc coding for the P-gp, responsible for the loss of cancerous cell sensitivity to chemotherapy.

II—RESULTS

1) Correlation Between Oncogenicity of Murine Fibroblast Cell Lines and the Measured Values of <<STAFI>> and $K_{obs}$.

FIG. 1 represents the determination of the value of delta mA max (<<STAFI>> corresponding to the quantity of polymerized actin in the steady state) in three binding murine parental cell lines, non-oncogenic (NIH 3T3 and NIH 3T3 EF zyxin) and oncogenic (NIH 3T3 EF). Table 2 below summarizes the kinetics of actin polymerization in the presence of cellular extracts by static fluorescence polarization.

TABLE 2

| Cell lines | Delta mA max | $K_{obs}$ |
| --- | --- | --- |
| NIH 3T3 | 65 | 0.086 |
| NIH 3T3 EF | 35 | 0.04 |
| NIH 3T3 zyxin | 57 | 0.033 |

The quantity of polymerized actin in the steady state (<<STAFI>>: fluorescence anisotropy value at the plateau) of the oncogenic line (NIH 3T3 EF) is compared to that of the non-oncogenic parental line (NIH 3T3) (FIG. 1). The delta mA max (STAFI) of the oncogenic line (NIH 3T3 EF) is distinctly lower than the delta mA max of the non-oncogenic line (NIH 3T3), i.e., 35 and 65 respectively.

The expression of the zyxin in the oncogenic line NIH 3T3 EF leads to an important reduction in the oncogenicity of this line (NIH 3T3 EF zyxin). The reduction in the oncogenicity of this line is correlated with the restoration of the delta mA max to a value near that of the reference line, in this case, the NIH 3T3 line, i.e., 57 and 65 respectively.

2) Correlation Between the Oncogenicity of Non-Binding Re-Lymphocytary Murine Cell Lines and the Measured Values of <<STAFI>> and $K_{obs}$.

Figure 2:
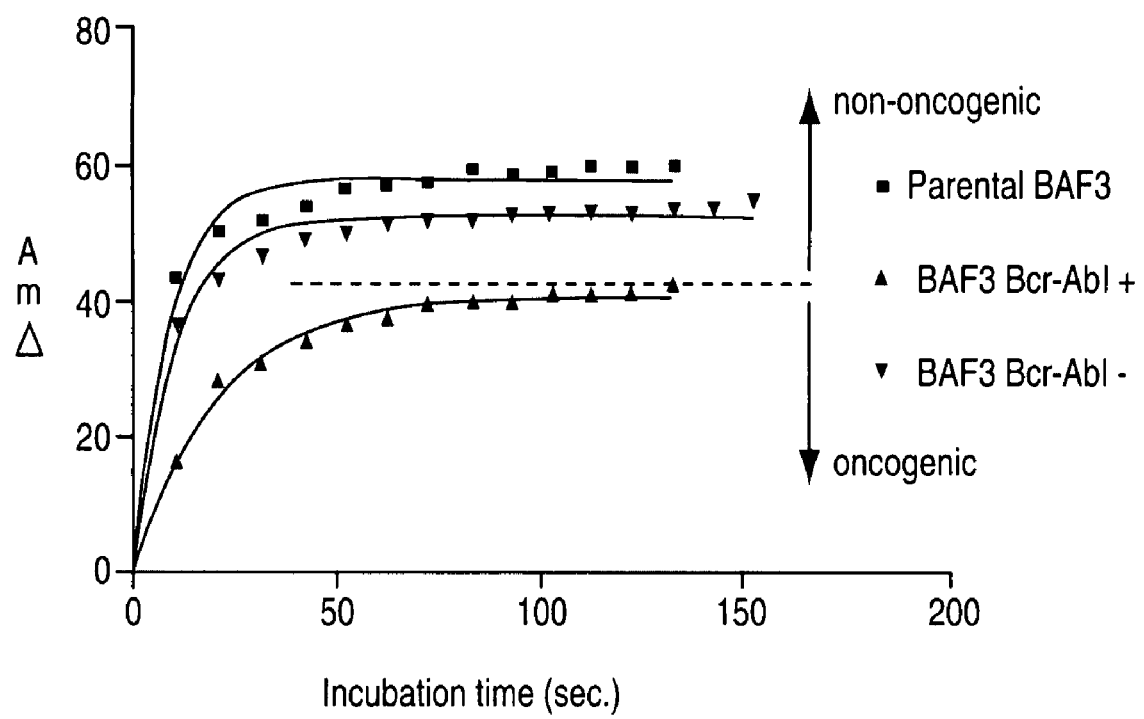
FIG. 2 illustrates actin polymerization in the steady state (<<STAFI>> delta mA max) in parental non-member cell lines (hematopoietic murine cells), non-tumor (BAF3 and BAF3 Bcr-Abl') and tumor (BAF3 Bcr-Abl').

FIG. 2 represents the determination of the value of delta mA max (<<STAFI>>, corresponding to the quantity of polymerized actin in the steady state) in different non-binding, non-oncogenic (parental BAF3, BAF3 Bcr-Abl') and oncogenic (BAF3 Bcr-Abl') cell lines. Table 3 summarizes the kinetics of actin polymerization in the presence of cellular extracts by static fluorescence polarization.

TABLE 3

| Cell lines | Delta mA max | $K_{obs}$ |
| --- | --- | --- |
| parental BAF3 | 58 | 0.12 |
| BAF3 Bcr-Abl | 40 | 0.05 |
| Bcr-Abl | 52 | 0.101 |

The quantity of polymerized actin in the steady state (<<STAFI>>: fluorescence anisotropy value at the plateau, that is the value of delta mA maximum) of the oncogenic line BAF3 Bcr-Abl' transformed by the fusion oncogene Bcr-Abl, is compared to that of the non-oncogenic parental line (BAF3) (FIG. 2) (Dugray, Geay et al. 2001). For the oncogenic line (BAF3 Bcr-Abl'), the delta mA max is distinctly lower than the delta mA max of the non-oncogenic line (BAF3), i.e., 40 and 58 respectively.

The same observation is made for the speed of actin polymerization, represented by the constant $K_{obs}$. For the oncogenic line (BAF3 Bcr-Abl'), $K_{obs}$ is distinctly lower than the $K_{obs}$ of the non-oncogenic line (BAF3), i.e., 0.05 and 0.12 respectively.

The repression of the oncogene fusion expression by the doxicycline in the BAF3 Bcr-Abl line leads to the loss of the oncogenicity of this line (Dugray, Geay et al. 2001). The repression of the oncogene expression restores the delta mA max of this oncogenic line to a value close to that of the non-oncogenic reference line, i.e., 52 and 58 respectively.

3) Correlation Between the Sensitivity to an Anti-Cancer Treatment of Lines of Human Mammary Carcinoma and the Measured Values of <<STAFI>> and $K_{obs}$.

Figure 3:
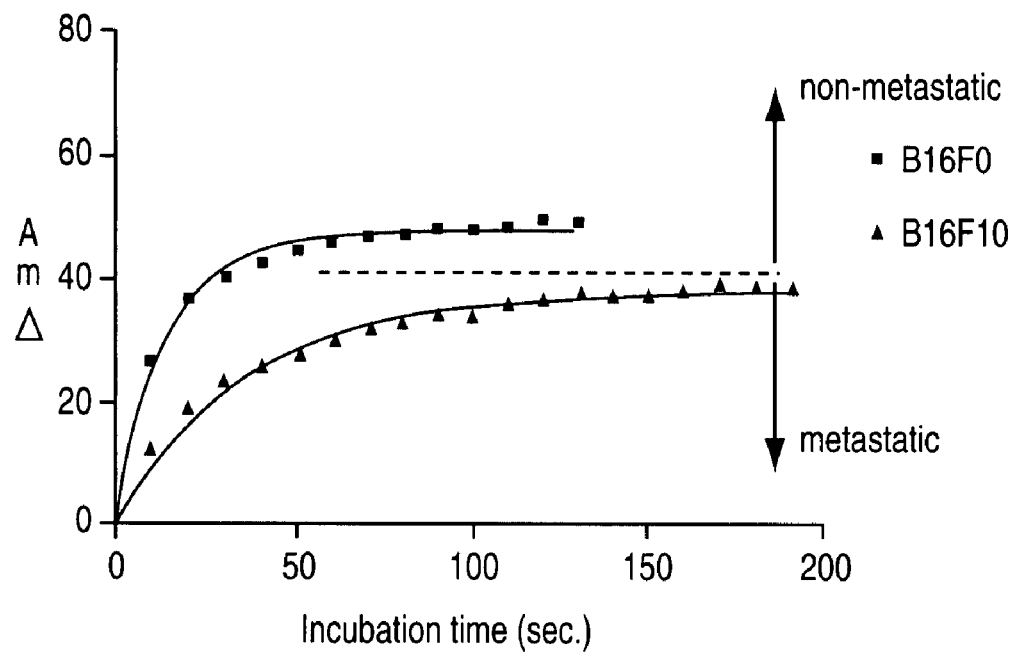
FIG. 3 illustrates the measurement of actin polymerization in the steady state (<<STAFI>>=delta mA max) in parental cell lines from breast carcinoma, sensitive (MCF7) and resistant (MCF7-Doxorubicin and MCF7-MDR).

FIG. 3 represents the determination of the value of delta mA max (<<STAFI>>, corresponding to the quantity of polymerized actin in the steady state) in two parental melanoma cell lines, with more or less metastatic potential (B16F0<B16F10). Table 4 below summarizes the kinetics of actin polymerization in the presence of cellular extracts by static fluorescence polarization.

TABLE 4

| Cell lines | Delta mA max | $K_{obs}$ |
| --- | --- | --- |
| B16F0 | 47 | 0.071 |
| B16F10 | 37 | 0.028 |

The quantity of polymerized actin in the steady state (<<STAFI>>: fluorescence anisotropy value at the plateau, that is the value of delta mA maximum) of the MCF7-Dox line, resistant to doxorubicin, is compared to that of the sensitive parental line (MCF7) (FIG. 3). For the resistant line (MCF7Dox), the delta mA max is distinctly lower than the delta mA max of the sensitive line (MCF7), i.e., 52 mA and 71 mA respectively.

In addition, the value of delta mA max of the resistant line MCF7-MDR, transfected by the gene coding for P-gp, is also comparable to the value of the sensitive line (MCF7). For the resistant line (MCF7-MDR), the delta mA max is also very distinctly lower than the delta mA max of the sensitive line (MCF7), i.e., 35 and 71 respectively.

4) Correlation Between the Metastatic Potential of Murine Melanoma Cell Lines (B16F0 and B16F10 and the Measured Values of <<STAFI>> and $K_{obs}$.

Figure 4:
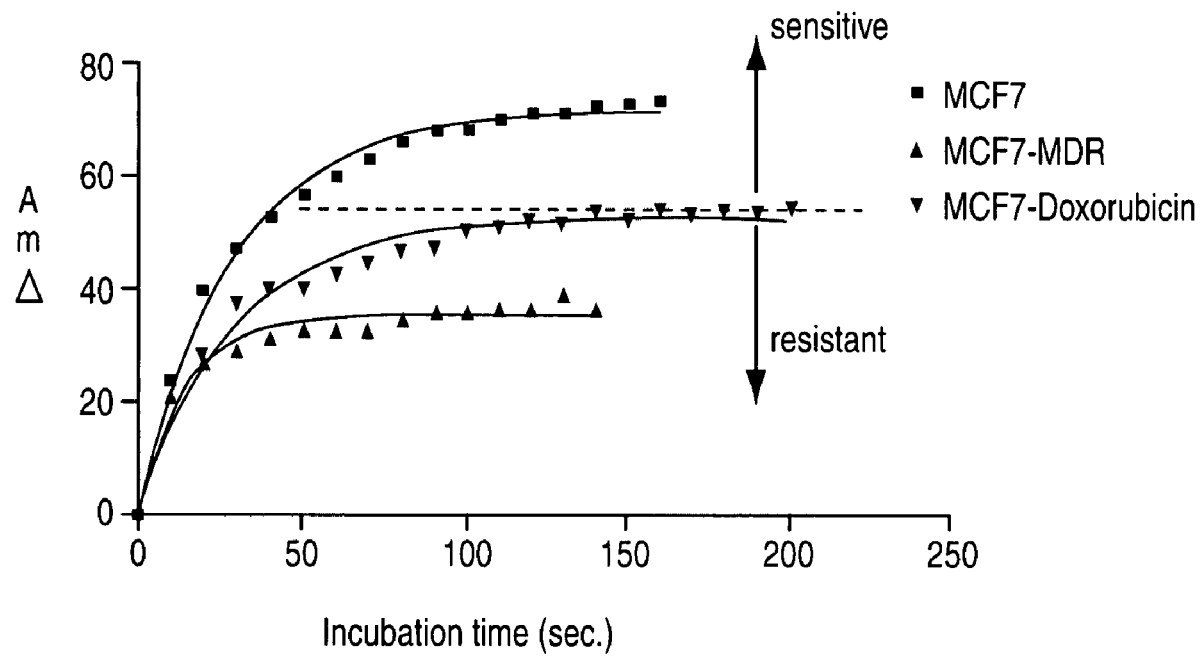
FIG. 4 illustrates the measurement of actin polymerization in the steady state (<<STAFI>>=delta mA max) in parental cell lines melanoma, with more or less metastatic potential (B16F0<B16F10).

FIG. 4 represents the determination of the value of delta mA max (<<STAFI>>, corresponding to the quantity of polymerized actin in the steady state) in different binding, sensitive (MCF7) and resistant (MCF7 Dox and MCF7 MDR) cell lines to an anti-cancer treatment. Table 5 below summarizes the kinetics of actin polymerization in the presence of cellular extracts by static fluorescence polarization.

TABLE 5

| Cell lines | Delta mA max | $K_{obs}$ |
|---|---|---|
| MCF7 | 71 | 0.0034 |
| MCF7-Doxorubicin | 52 | 0.0034 |
| MCF7 MDR | 35 | 0.071 |

The quantity of polymerized actin in the steady state (<<STAFI>>: fluorescence anisotropy value at the plateau, that is, the value of delta MA maximum) of the B16F10 line, selected for its metastatic potential starting with the B16F0 line (Nakamura, Yoshikawa et al. 2002), is compared to that of the less metastatic parental line (B16F0) (FIG. 4). For the most aggressive line (B16F10), the delta mA max is distinctly lower than the delta mA max of the nononcogenic line B16F0), i.e., 37 and 47 respectively.

The same observation is made for the speed of actin polymerization, represented by the constant $K_{obs}$. For the most aggressive line (B16F10), $K_{obs}$ is distinctly lower than the $K_{obs}$ of the less aggressive line (B16F0), i.e., 0.028 and 0.071 respectively.

5) Identification of Jasplakinolide as a Molecule which Restores the Actin Polymerization Potential at the Steady State.

Figure 5:
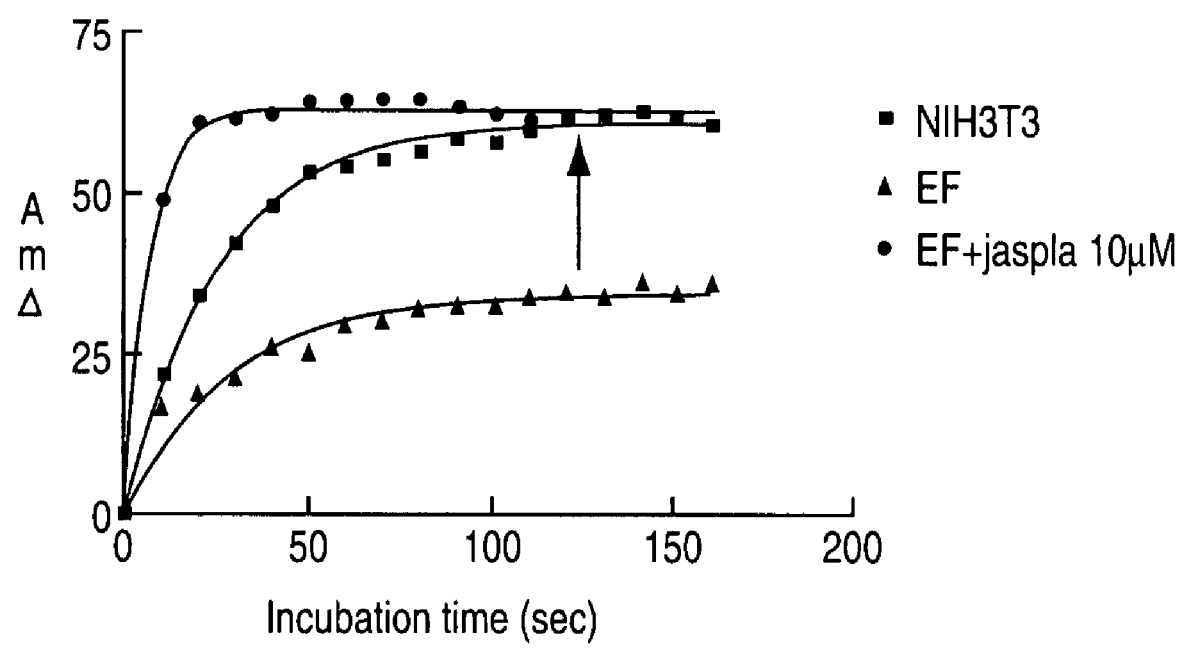
FIG. 5 illustrates the identification of a molecule (the jasplakinolide) capable of restoring the quantity of actin in the steady state (<<STAFI>>=delta mA max) of an oncogenic line to the level of the quantity of a non-oncogenic line.

FIG. 5 represents the restoration of the value of delta mA max (<<STAFI>>, corresponding to the quantity of polymerized actin in the steady state) of oncogenic cells (NIH 3T3 EF, marked EF) to the level of the value of non-oncogenic cells (NIH 3T3) by the addition of jasplakinolide (marked jaspla).

The quantity of polymerized actin in the steady state (<<STAFI>>: fluorescence anisotropy value at the plateau, that is, the value of delta mA maximum) of oncogenic cells (NIH 3T3 EF, marked EF) was measured after the addition of 10 µM of jasplakinolide to the polymerization medium. The delta mA max of tumor cells determined at an initial value of 35 mA is restored by the addition of jasplakinolide to a value close to that of the non-oncogenic line (NIH 3T3), 66 mA and 65 mA respectively.

The same observation is made for the speed of actin polymerization, represented by the constant. Jasplakinolide restores the $K_{obs}$ to a value equal to 0.04, near a value that is close to the value obtained with non-oncogenic cells, i.e., 0.15 and 0.086 respectively.

BIBLIOGRAPHIC REFERENCES

1) Damiano, J. S., L. A. Hazlehurst, et al. (2001). "Cell adhesion-mediated drug resistance (CAM-DR) protects the K562 chronic myelogenous leukemia cell line from apoptosis induced by BCR/ABL inhibition, cytotoxic drugs, and gamma-irradiation." *Leukemia* 15(8): 1232-9.
2) called Faute, M. A., L. Laurent, et al. (2002). "Distinctive alterations of invasiveness, drug resistance and cell-cell organization in 3D cultures of NCF-7, a human breast cancer cell line, and its multidrug resistant variant." *Clin Exp Metastasis* 19(2): 161-8.
3) Dugray, A., J. F., Geay, et al. (2001). "Rapid generation of a tetracycline-inducible BCR-ABL defective retrovirus using a single autoregulatory retroviral cassette." *Leukemia* 15: 1658-62.
4) Fradelizi, J., V. Noireaux, et al. (2001). "ActA and human zyxin harbour Arp2/3-independent acting polymerization activity." *Nat Cell Biol* 3(8) 699-707.
5) Lopes, E. C., G. Ernst, et al. (2001), Dissimilar invasive and metastatic behavior of vincriatine and doxorubicin-resistant cell lines derived from a murine T cell lymphoid leukemia." *Clin Exp Metastasis* 19(4): 283-90.
6) Machesky, L. M., R. D. Mullins, et al. (1999). "Scar, a WASp-related protein, activates nucleation of actin filaments by the Arp2/3 complex." *Proc Natl Acad Sci USA* 96(7): 3739-44.
7) Mitsumoto, M., T. Kamura, et al. (1998). "Emergence of higher levels of invasive and metastatic properties in the drug-resistant cancer cell lines after the repeated administration of cisplatin in tumor-bearing mice." *J Cancer Res Clin Oncol* 124(11): 607-14.
8) Nakamura, K., N. Yoshikawa, et al. (2002). "Characterization of murine melanoma cell lines by their mortal malignancy using an experimental metastatic modal." *Life Sci* 70(7): 791-8.

The invention claimed is:

1. Method of analysis of the tumor aggressivity of cancerous cells comprising the real time measurement of the quantity of polymerized actin in the steady state in a lysate of the said cells wherein the real time measurement of the quantity of actin in the steady state is carried out by static fluorescence polarization in the presence of actin monomers bound to a fluorochrome, the monomers being incorporated into the actin filaments (actin F) formed during the endogenous actin polymerization of the lysate.

2. Method according to claim 1, wherein the measurement carried out on the lysate is compared to one or more reference values of the quantity of polymerized actin in the steady state.

3. Method according to claim 1, wherein the quantity of polymerized actin corresponds to the sum of all the F-form actin.

4. Method according to claim 1, wherein the actin monomers bound to a fluorochrome are added to the cellular lysate in a proportion ranging between $1/80^{th}$ and $1/1600^{th}$ in relation to the quantity of endogenous actin.

5. Method according to claim 1, including the steps of:
   lysing cancerous cells in non-denaturing conditions for the proteins, and the eliminating cellular debris,
   determining the total amount of proteins in the lysate,
   adding actin monomers bound to a fluorochrome,
   adding one or more substances to activate endogenous actin polymerization and protect the lysate proteins, wherein said substances are selected from the group consisting of the Arp2/3 complex and the Ena/VASP family of proteins, and
   measuring the quantity of polymerized actin in the steady state in the lysate.

6. Method of identification of molecules likely to present an anti-cancer activity, comprising implementing a method according to one of claims 1-3 and 4-5 in the presence of said molecule, and determining the capacity of said molecule to restore a quantity of polymerized actin in the steady state corresponding to that of non-aggressive cells is determined.

7. A method of evaluating cancer cells to determine their invasiveness, comprising carrying out the method according to one of claims 1-3 and 4-5.

8. A method of evaluating cancer cells to determine their oncogenicity, comprising carrying out the method according to one of claims 1-3 and 4-5.

9. A method of evaluating cancer cells to determine their sensitivity to an anti-cancer treatment, comprising carrying out the method according to one of claims 1-3 and 4-5.

10. The method according to claim 9, wherein the said anti-cancer treatment consists of radiotherapy or chemotherapy.

* * * * *